(12) United States Patent
Ratner et al.

(10) Patent No.: US 11,918,718 B2
(45) Date of Patent: Mar. 5, 2024

(54) MOLECULARLY IMPRINTED POLYMERS FOR REMOVAL OF TRIMETHYLAMINE N-OXIDE

(71) Applicant: University of Washington, Seattle, WA (US)

(72) Inventors: Buddy D. Ratner, Seattle, WA (US); Runbang Tang, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 18/056,994

(22) Filed: Nov. 18, 2022

(65) Prior Publication Data

US 2023/0173459 A1 Jun. 8, 2023

Related U.S. Application Data

(62) Division of application No. 16/837,828, filed on Apr. 1, 2020, now Pat. No. 11,524,275.

(60) Provisional application No. 62/828,340, filed on Apr. 2, 2019.

(51) Int. Cl.
| | |
|---|---|
| *B01J 20/26* | (2006.01) |
| *A61M 1/16* | (2006.01) |
| *B01D 15/38* | (2006.01) |
| *B01J 20/28* | (2006.01) |

(52) U.S. Cl.
CPC ........ *A61M 1/1696* (2013.01); *B01D 15/3852* (2013.01); *B01J 20/267* (2013.01); *B01J 20/268* (2013.01); *B01J 20/28004* (2013.01)

(58) Field of Classification Search
CPC . A61M 1/1696; B01D 15/3852; B01J 20/267; B01J 20/268; B01J 20/28004
See application file for complete search history.

(56) References Cited

U.S. PATENT DOCUMENTS

2013/0011364 A1 1/2013 Fichert et al.

FOREIGN PATENT DOCUMENTS

| WO | 2010/081076 A3 | 7/2010 |
| WO | 2018/211389 A1 | 11/2018 |
| WO | WO-2018211389 A1 * | 11/2018 |

OTHER PUBLICATIONS

Konishi, A., et al., "A Molecularly Imprinted Polymer-modified Potentiometri Sensor for the Detection of Glutathione," The Japan Society for Analytical Chemistry, vol. 35 1111-1115, Oct. 2019.

Liang, S., et al., "Molecularly Imprinted Phloroglucinol-Formaldehyde-Melamine Resin Prepared in a Deep Eutectic Solvent for Selective Recognition of Clorprenaline and Bambuterol in Urine," Analytica Chimica Acta 951, 68-77, Nov. 2016.

Saran, R., "US Renal Data System 2016 Annual Data Report: Epidemiology of Kidney Disease in the United States," American Journal of Kidney Diseases 69(3): SVII-SVIII, 2017.

Shi, T., "Advancing the Sensitivity of Selected Reaction Monitoring-Based Targeted Quantitative Proteomics," Proteomics, vol. 12 1074-1092, 2012.

Zhang, "Synthesis of Molecularly Imprinted Polymer Nanoparticles for the Fast and Highly Selective Adsorption of Sunset Yellow," Journal of Separation Science vol. 39 1559-1566, 2016.

* cited by examiner

*Primary Examiner* — Yong L Chu
(74) *Attorney, Agent, or Firm* — Christensen O'Connor Johnson Kindness PLLC

(57) ABSTRACT

The present disclosure features a composition, including molecularly imprinted crosslinked polymers that have been imprinted with trimethylamine N-oxide. The molecularly imprinted crosslinked polymers have specific binding sites for trimethylamine N-oxide, and a trimethylamine N-oxide absorption capacity of at least 0.5 mg/g.

5 Claims, 7 Drawing Sheets

MOLECULARLY IMPRINTED POLYMERS FOR REMOVAL OF TRIMETHYLAMINE N-OXIDE

CROSS-REFERENCES TO RELATED APPLICATIONS

This application is a divisional of application Ser. No. 16/837,828, filed Apr. 1, 2020, now U.S. Pat. No. 11,524,275, which claims the benefit of U.S. Patent Application No. 62/828,340, filed Apr. 2, 2019, the entire disclosures of which are hereby incorporated by reference in its entirety.

BACKGROUND

End stage renal disease (ESRD), or kidney failure, affects more than 660,000 Americans. The majority of them (about 420,000) depend on hemodialysis three times per week and 3-5 hours each time to sustain their lives. The annual cost of hemodialysis in the U.S. is about 42 billion dollars. Traditional hemodialysis requires ESRD patients to be tethered to the dialysis machine about the size of a refrigerator, which confines patients' lives to dialysis facilities. In addition, the intermittent nature of hemodialysis is far from the physiological condition where the blood is continuously filtered by the kidney. Portable or even wearable hemodialysis machines will liberate ESRD patients and provide continuous dialysis comparable to physiological condition. The major obstacle towards this goal is to reduce the weight and volume of the current dialysis machines. Specifically, the dialysate consumption for a traditional dialysis is about 120 L at each session. Dialysate storage limits the potential of portable hemodialysis machines. Removing specific toxins from the dialysate and recycling dialysate may ultimately overcome a major obstacle towards portable hemodialysis machines.

Thus, there is a need for a composition and method for selective and efficient removal of toxins, such as trimethylamine nitrogen oxide, from a dialysate. The present disclosure fulfills these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a composition, including a crosslinked polymer derived from: a monomer including a ($C_{0-6}$alkyl)acrylic acid, di($C_{1-6}$alkyl)acrylic acid, or a combination thereof; and a crosslinker including a ($C_{1-6}$ alkylene glycol)-di($C_{1-6}$alkyl)acrylate, trimethylolpropane trimethacrylate, N,N'-methylenebisacrylamide, or any combination thereof. The crosslinked polymer is a trimethylamine N-oxide molecularly imprinted polymer (TMAO MIP), has specific binding sites for trimethylamine N-oxide, and has a trimethylamine N-oxide absorption capacity of at least 0.5 mg/g.

In another aspect, the present disclosure features a method of removing trimethylamine N-oxide from a hemodialysis dialysate, including passing the hemodialysis dialysate including trimethylamine N-oxide through the crosslinked polymer (i.e., the TMAO MIP) described herein, and absorbing the trimethylamine N-oxide onto the crosslinked polymer to remove the trimethylamine N-oxide from the hemodialysis dialysate.

In yet another aspect, the present disclosure features a method of making a crosslinked polymer, including polymerizing a monomer including a ($C_{0-6}$alkyl)acrylic acid, di($C_{1-6}$alkyl)acrylic acid, or any combination thereof; and a crosslinker including a ($C_{1-6}$ alkylene glycol)-di($C_{1-6}$alkyl)acrylate, trimethylolpropane trimethacrylate, N,N'-methylenebisacrylamide, or any combination thereof, at a monomer:crosslinker ratio of from 1:9 to 14:1, in the presence of trimethylamine N-oxide (a template) and a solvent, to provide the crosslinked polymer (the trimethylamine N-oxide molecularly imprinted polymer). The crosslinked polymer includes specific binding sites for trimethylamine N-oxide and a trimethylamine N-oxide absorption capacity of at least 0.5 mg/g.

In yet a further aspect, the present disclosure features a chromatography column or chromatography cartridge, including a plurality of particles including a crosslinked polymer derived from a monomer including a ($C_{0-6}$alkyl)acrylic acid, di($C_{1-6}$alkyl)acrylic acid, or any combination thereof; and a crosslinker including a ($C_{1-6}$ alkylene glycol)-di($C_{1-6}$alkyl)acrylate, trimethylolpropane trimethacrylate, N,N'-methylenebisacrylamide, or any combination thereof. The crosslinked polymer is a trimethylamine N-oxide molecularly imprinted polymer (TMAO MIP), has specific binding sites for trimethylamine N-oxide, and a trimethylamine N-oxide absorption capacity of at least 0.5 mg/g. The particles have an average diameter of from 300 nm to 2000 nm.

DESCRIPTION OF THE DRAWINGS

The foregoing aspects and many of the attendant advantages of the subject matter of the present disclosure will become more readily appreciated as the same become better understood by reference to the following detailed description, when taken in conjunction with the accompanying drawings, wherein.

DETAILED DESCRIPTION

Figure 1:
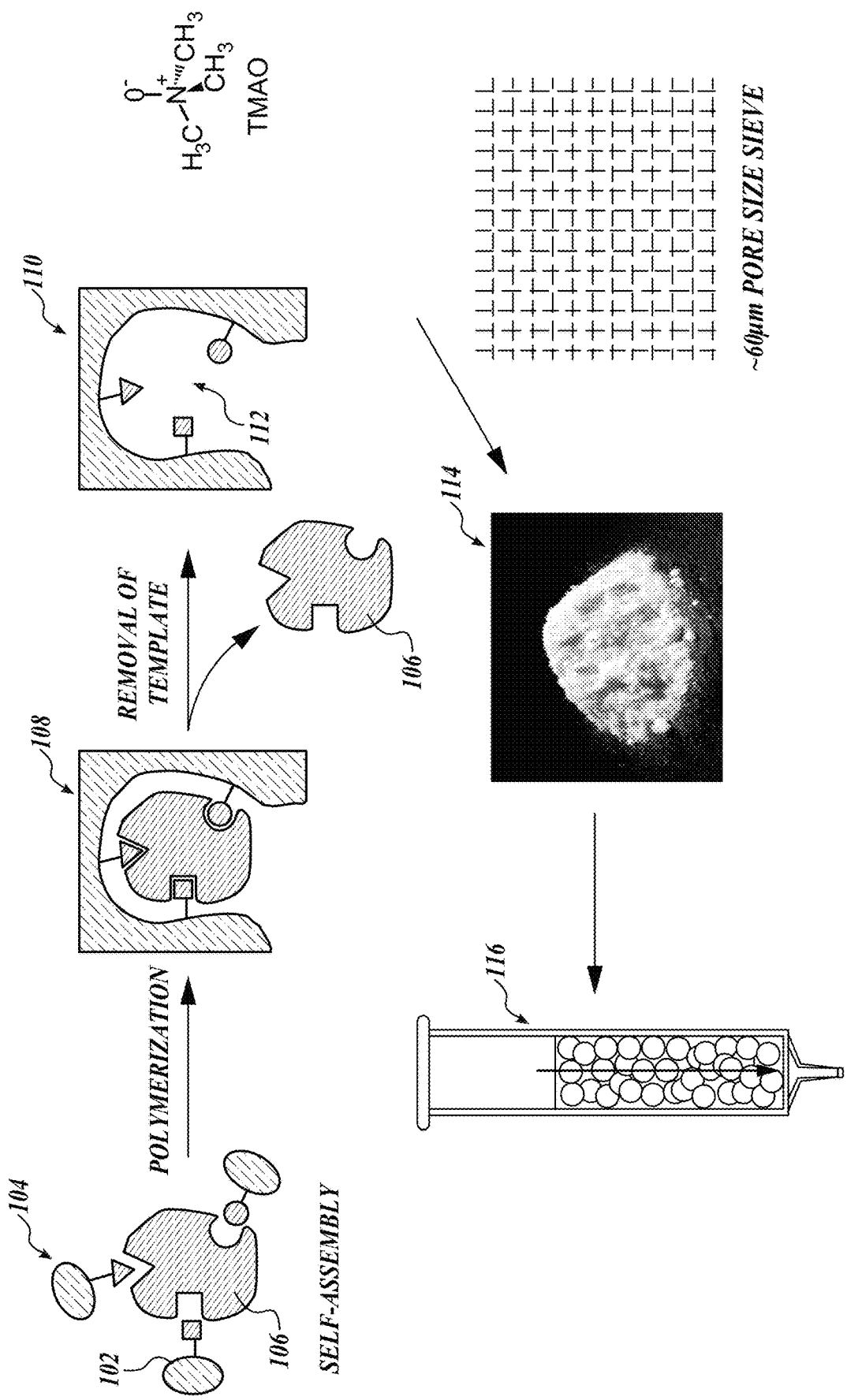
FIG. 1 is a schematic showing an exemplary synthesis of trimethylamine nitrogen oxide (TMAO) molecularly imprinted polymer, and showing the structure of a TMAO template.

Molecularly imprinted polymers (MIPs) are synthetic "antibody mimics" with high specificity, excellent stability, and low cost. In the present disclosure, MIPs are used for removal of trimethylamine nitrogen oxide (TMAO) in dialysate by targeted removal of key toxins with little effect on other components of the dialysate. In particular, the present disclosure demonstrates that MIPs imprinted with TMAO, a uremic toxin in the plasma of subjects with compromised kidney function (e.g., end stage renal disease ESRD patients), can remove TMAO efficiently and selectively from a dialysate.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

As used herein, "specific binding" or "binding specificity" or "specificity" in the context of binding by MIPs refers to a preferential binding to a given molecule or target for which the MIP is designed for (e.g., TMAO) compared to a comparative molecule having a similar size and dipole moment (e.g., DMSO), or compared to other toxins in a hemodialysis dialysate.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, the term "random copolymer" is a copolymer having an uncontrolled mixture of two or more constitutional units. The distribution of the constitutional units throughout a polymer backbone can be a statistical distribution, or approach a statistical distribution, of the constitutional units. In some embodiments, the distribution of one or more of the constitutional units is favored.

As used herein, the term "constitutional unit" of a polymer refers to an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be —$CH_2CH_2O$— corresponding to a repeat unit, or —$CH_2CH_2OH$ corresponding to an end group.

As used herein, the term "repeat unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

As used herein, the term "hydrodynamic diameter" refers to the apparent size of particle assemblies hydrated in a solvent (e.g., water), as measured by dynamic light scattering.

As used herein, a "crosslinker" is molecule containing two or more reactive functional groups that are separated at various lengths. The reactive functional groups covalently react with two or more functionalities on one or more polymer strands to covalently bond the functionalities together to form a crosslink.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Crosslinked Molecularly Imprinted Polymers

Referring to FIG. 1, the MIPs of the present disclosure can be made by first assembling monomers 102 and crosslinkers 104 in the presence of a TMAO template 106, the chemical structure of which is shown in FIG. 1. The monomers 102 and crosslinkers 104 can be polymerized to provide a polymer matrix 108 surrounding the TMAO template 106, and the TMAO template 106 can then be removed (e.g., by washing with a solvent in which the TMAO is soluble but in which the resulting polymer is insoluble) to provide the molecularly imprinted crosslinked polymer 110, which can be in the form of a powder 114 or processed into a powder 114. The powder 114 can be in the form of microspheres or nanosphere of polymer 110. The powder 114 can then be incorporated into a column or a cartridge 116, which can be integrated into a hemodialysis circuit (not shown) to remove TMAO from a dialysate.

As an example, MIPs for TMAO can be synthesized starting from a reaction mixture including TMAO which serves as a template, monomers (e.g., methacrylic acid), crosslinkers (e.g., ethylene glycol dimethacrylate), and one or more solvents. The reaction mixture can include a radical polymerization initiator, such as azobisisobutyronitrile (AIBN), and optionally a porogen. The reaction mixture can be heated under inert atmosphere for a period of time to provide the MIP. For example, the reaction mixture can be heated at a temperature of about 60° C. (e.g., from 30° C. to 100° C., from 45° C. to 100° C., from 60° C. to 90° C., from 60° C. to 75° C., about 50° C., about 55° C., about 65° C., or about 75° C.) for about 24 hours (e.g., about 20 hours, about 15 hours, about 12 hours, or about 6 hours) under $N_2$ or argon, to provide the MIP. In some embodiments, rather than heating the reaction mixture, the reaction mixture can be irradiated with ultraviolet light in the presence of a photoinitiator to provide the MIP. The MIP can be formed in situ as a nanoparticle or microparticle during synthesis, and/or the MIP can be processed into a powder after synthesis. The MIP powder can be evaluated for TMAO absorption, for example, using high performance liquid chromatography (HPLC), in tandem with mass spectroscopy (MS).

In some embodiments, the present disclosure features a composition, including a MIP (also referred to herein as a crosslinked polymer, or a crosslinked MIP) derived from: a monomer such as $(C_{0-6}alkyl)$acrylic acid, $di(C_{1-6}alkyl)$ acrylic acid, and/or a combination thereof; and a crosslinker such as $(C_{1-6}$ alkylene glycol$)$-$di(C_{1-6}alkyl)$acrylate, trimethylolpropane trimethacrylate, and/or N,N'-methylenebisacrylamide. The crosslinked MIP has been imprinted with trimethylamine N-oxide. The crosslinked MIP has specific binding sites for trimethylamine N-oxide and a trimethylamine N-oxide absorption capacity of at least 0.5 mgs/g.

In some embodiments, when the monomer is $di(C_{1-6}alkyl)$ acrylic acid, the two $C_{1-6}$ alkyl groups can be the same or different, such that each $C_{1-6}$ alkyl group is independently selected from $C_1$ alkyl, $C_2$ alkyl, $C_3$ alkyl, $C_4$ alkyl, $C_5$ alkyl, or $C_6$ alkyl.

In some embodiments, the monomer is methylacrylic acid, ethylacrylic acid, propylacrylic acid, butylacrylic acid, pentylacrylic acid, hexylacrylic acid, dimethylacrylic acid, diethylacrylic acid, and/or dipropyl acrylic acid. In some embodiments, the monomer is methylacrylic acid, ethylacrylic acid, propylacrylic acid, butylacrylic acid, pentylacrylic acid, hexylacrylic acid, dimethylacrylic acid, and/or diethylacrylic acid. In some embodiments, the monomer is methylacrylic acid, ethylacrylic acid, and/or dimethylacrylic acid. In certain embodiments, the monomer is methylacrylic acid and/or dimethylacrylic acid. In some embodiments, the monomer is acrylic acid and/or methacrylic acid. In certain embodiments, the monomer is methylacrylic acid.

In some embodiments, the crosslinker is $(C_{1-6}$ alkylene glycol$)$-$di(C_{1-6}alkyl)$acrylate, or trimethylolpropane trimethacrylate. In some embodiments, the crosslinker is ethylene glycol dimethacrylate, propylene glycol dimethacrylate, 1,4-butylene glycol dimethacrylate, 1,3-butylene glycol dimethacrylate, or any combination thereof. In some embodiments, the crosslinker is ethylene glycol dimethacrylate.

In some embodiments, the MIP is in the form of a plurality of particles, the particles having an average diameter of from 300 nm to 2000 nm (e.g., from 300 nm to 1500 nm, from 300 nm to 1000 nm, or from 300 nm to 800 nm), as determined by scanning electron microscopy.

In some embodiments, the MIP is derived from a monomer to crosslinker ratio of from 14:1 to 1:9 (e.g., 10:1 to 1:5; 10:1 to 1:1; 10:1 to 5:1; 10:1; or 8:1). In some embodiments, the monomer is present at a mole percentage of at least 10% (e.g., at least 20%, at least 30%, at least 40%, at least 50%, at least 60%, at least 70%, at least 80%, at least 90%, at least 92%) and/or at most 95% (at most 94%, at most 92%, at most 90%, at most 80%, at most 70%, at most 60%, at most 50%, at most 40%, at most 30%, or at most 20%), relative to the total moles of the crosslinker(s) and monomer(s). In certain embodiments, the monomer is present at a mole percentage of about 89% (e.g., about 90%, or about 94%), relative to the total moles of the crosslinker(s) and monomer(s).

In some embodiments, the crosslinker is present at a mole percentage of at least 5% (e.g., at least 6%, at least 8%, at least 10%, at least 20%, at least 30%, at least 40%, at least 50%, at least 60%, at least 70%, at least 80%) and/or at most 90% (e.g., at most 80%, at most 70%, at most 60%, at most 50%, at most 40%, at most 30%, at most 20%, at most 10%, at most 8%, or at most 6%), relative to the total moles of the crosslinker(s) and monomer(s). In certain embodiments, the crosslinker is present at a mole percentage of about 11% (e.g., about 10%, or about 6%), relative to the total moles of the crosslinker(s) and monomer(s).

In some embodiments, the MIP has a trimethylamine N-oxide absorption capacity of 0.075 mg/g or more (e.g., 0.1 mg/g or more, 0.2 mg/g or more, 0.3 mg/g or more, 0.4 mg/g or more, 0.5 mg/g or more, 0.6 mg/g or more, 0.7 mg/g or more, 0.8 mg/g or more, or 0.9 mg/g or more) and/or 1.05 mg/g or less (e.g., 0.9 mg/g or less, 0.8 mg/g or less, 0.7 mg/g or less, 0.6 mg/g or less, 0.5 mg/g or less, 0.4 mg/g or less, 0.3 mg/g or less, 0.2 mg/g or less, or 0.1 mg/g or less). In some embodiments, the MIP has a trimethylamine N-oxide absorption capacity of 0.5 mg/g or more. In some embodiments, the MIP a trimethylamine N-oxide absorption capacity of about 1 mg/g (e.g., 1.05 mg/g). The absorption capacity can be related to the ratio of the monomer to crosslinker in the MIP. For example, a crosslinked MIP having a monomer to crosslinker ratio of 8:1 can have a TMAO absorption capacity of about 1.05 mg/g. As another example, a crosslinked MIP having a monomer to crosslinker ratio of 8:1 can have a TMAO absorption capacity of about 1.05 mg/g, when the monomer is MAA and the crosslinker is EGDMA. As another example, a crosslinked MIP having a monomer to crosslinker ratio of 1:9 can have a TMAO absorption capacity of about 0.075 mg/g, when the monomer is MAA and the crosslinker is EGDMA.

The crosslinked MIP, or particles of the crosslinked MIP, selectively (e.g., more preferentially) and more efficiently bind to TMAO compared to other molecules with similar steric and electronic properties (e.g., dipole moment). For example, the crosslinked polymer, or a plurality of particles formed of the crosslinked polymer can have a lower dimethyl sulfoxide (DMSO) absorption compared to TMAO absorption. In some embodiments, when exposed to a dialysate having equal amounts of TMAO and DMSO, a higher proportion of TMAO is absorbed by the MIP of the present disclosure compared to DMSO (e.g., 20 fold more, 10 fold more, or 5 fold more compared to DMSO). In some embodiments, the crosslinked MIP, or particles of the crosslinked MIP, has a dimethyl sulfoxide absorption capacity of 0.11 mg/g (1.4 μmol/g) or less (e.g., 0.05 mg/g or less, or 0.01 mg/g or less).

The present disclosure also features a method of removing trimethylamine N-oxide from a hemodialysis dialysate, including passing the hemodialysis dialysate including trimethylamine N-oxide through the crosslinked MIP described above, or through particles formed of the crosslinked MIP described above, and absorbing the trimethylamine N-oxide onto the crosslinked MIP to remove the trimethylamine N-oxide from the hemodialysis dialysate. The crosslinked MIP can be regenerated by removing the absorbed trimethylamine N-oxide. For example, to regenerate absorption capacity, the absorbed trimethylamine N-oxide can be removed from the crosslinked polymer by washing the polymer with a solvent (e.g., deionized water, methanol, ethanol, a 0.01 M sulfuric acid aqueous solution, an aqueous buffer, and/or a dialysate) that dissolves the trimethylamine N-oxide, but not the crosslinked polymer.

As discussed above, the crosslinked MIP can be in the form of a plurality of particles. The plurality of particles can be packed into a chromatography column or a chromatography cartridge. In use, a hemodialysis dialysate can pass through the chromatography column or cartridge. In some embodiments, the hemodialysis dialysate is passed through the chromatography column or a chromatography cartridge at a rate of 1 ml/minute or more (e.g., 10 ml/minute or more, 20 ml/minute or more, 30 ml/minute or more, 40 ml/minute or more, 50 ml/minute or more, 75 ml/minute or more, 100 ml/minute or more, 200 ml/minute or more, 300 ml/minute or more) and/or 400 ml/minute or less (e.g., 300 ml/minute or less, 200 ml/minute or less, 100 ml/minute or less, 75 ml/minute or less, 50 ml/minute or less, 40 ml/minute or less, 30 ml/minute or less, 20 ml/minute or less, or 10 ml/minute or less). In some embodiments, the hemodialysis dialysate is passed through the chromatography column or a chromatography cartridge at a rate of about 40 ml/minute (e.g., about 60 ml/minute, about 80 ml/minute, or about 100 ml/minute).

In some embodiments, the hemodialysis dialysate is passed through a filter to remove urea present in the hemodialysis dialysate prior to, concurrent with, or subsequent to passing the hemodialysis dialysate through the crosslinked MIP. For example, the hemodialysis dialysate can be passed through a filter to remove urea present in the hemodialysis dialysate prior to passing the hemodialysis dialysate through the crosslinked MIP.

In some embodiments, the hemodialysis dialysate can include one or more toxins complexed with albumin. In some embodiments, the toxin(s) complexed with albumin can be separated from the albumin. The toxin(s) complexed with albumin carried by the dialysate can be wholly or partially removed prior to, concurrent with, or subsequent to passing the hemodialysis dialysate through the crosslinked MIP. As discussed above, TMAO can be removed by the crosslinked MIP. In certain embodiments, the hemodialysis dialysate is first passed through a filter to remove urea, then through a filter to separate and/or remove albumin-bound toxins, and then through the crosslinked MIP to remove TMAO from the hemodialysis dialysate.

Methods of Making the Crosslinked Polymer

The present disclosure features a method of making a crosslinked MIP, including polymerizing a monomer such as a $(C_{0-6}$alkyl)acrylic acid, di$(C_{1-6}$alkyl)acrylic acid, or any combination thereof; and a crosslinker such as a $(C_{1-6}$ alkylene glycol)-di$(C_{1-6}$alkyl)acrylate, trimethylolpropane trimethacrylate, N,N'-methylenebisacrylamide, or any combination thereof, at a monomer:crosslinker ratio as described above (e.g., from 1:9 to 14:1); in the presence of trimethylamine N-oxide, which can serve as a template; and solvent; to provide the crosslinked MIP. The reaction mixture can include an optional porogen. The method can further include removing the trimethylamine N-oxide template from the crosslinked MIP, for example, by washing the crosslinked MIP with a solvent that dissolves the trimethylamine N-oxide but not the crosslinked MIP. The resulting crosslinked MIP has specific binding sites for trimethylamine N-oxide and has a trimethylamine N-oxide absorption capacity of at least 0.5 mg/g.

In some embodiments, the method further includes grinding the crosslinked MIP to form the plurality of particles of the crosslinked polymers. In certain embodiments, the crosslinked MIP is formed as particles in situ in a reaction mixture including the monomer, crosslinker, trimethylamine N-oxide, and a solvent. When the crosslinked MIP particles are formed in situ, the polymerization of the monomer and the crosslinker can be conducted in a dilute reaction mixture, for example, at a concentration of less than 180 mM (e.g., less than 200 mM, or less than 250 mM) to form a plurality of particles of the crosslinked MIP.

In some embodiments, the solvent is any solvent or mixtures thereof where the monomer and crosslinker are soluble, but the crosslinked MIP is not soluble. The solvent can be a pore-forming solvent, such that a crosslinked MIP formed in the solvent has pores that are generated in situ during polymerization. For example, the solvent can be acetonitrile, methanol, water, a dialysate, or any combination thereof.

In some embodiments, the optional porogen can be a sacrificial solid, such as sodium chloride, polymethylmethacrylate microspheres, and/or polymethylmethacrylate nanospheres, which can be removed from the crosslinked MIP after the crosslinked MIP has been formed.

In some embodiments, the reaction mixture including the monomer, crosslinker, trimethylamine N-oxide, solvent, and the optional porogen can further include a radical initiator. For example, the radical initiator can include azobisisobutyronitrile, benzoyl peroxide, ammonium persulfate with N,N,N'N'-tetramethylethylenediamine (TEMED). In some embodiments, the reaction mixture can include a photoinitiator, and the reaction (i.e., polymerization) can be carried out under ultraviolet illumination.

Assembly

The present disclosure also features a chromatography column or chromatography cartridge, including a plurality of particles including a crosslinked MIP described above. As discussed above, the crosslinked MIP can be derived from, for example, a monomer including a ($C_{0-6}$alkyl)acrylic acid, di($C_{1-6}$alkyl) acrylic acid, or any combination thereof; and a crosslinker comprising a ($C_{1-6}$ alkylene glycol)-di($C_{1-6}$alkyl)acrylate, trimethylolpropane trimethacrylate, N,N'-methylenebisacrylamide, or any combination thereof. The crosslinked MIP includes specific binding sites for trimethylamine N-oxide and a trimethylamine N-oxide absorption capacity of at least 0.5 mg/g. The particles including crosslinked MIP have an average diameter of from 300 nm to 2000 nm.

Figure 2:
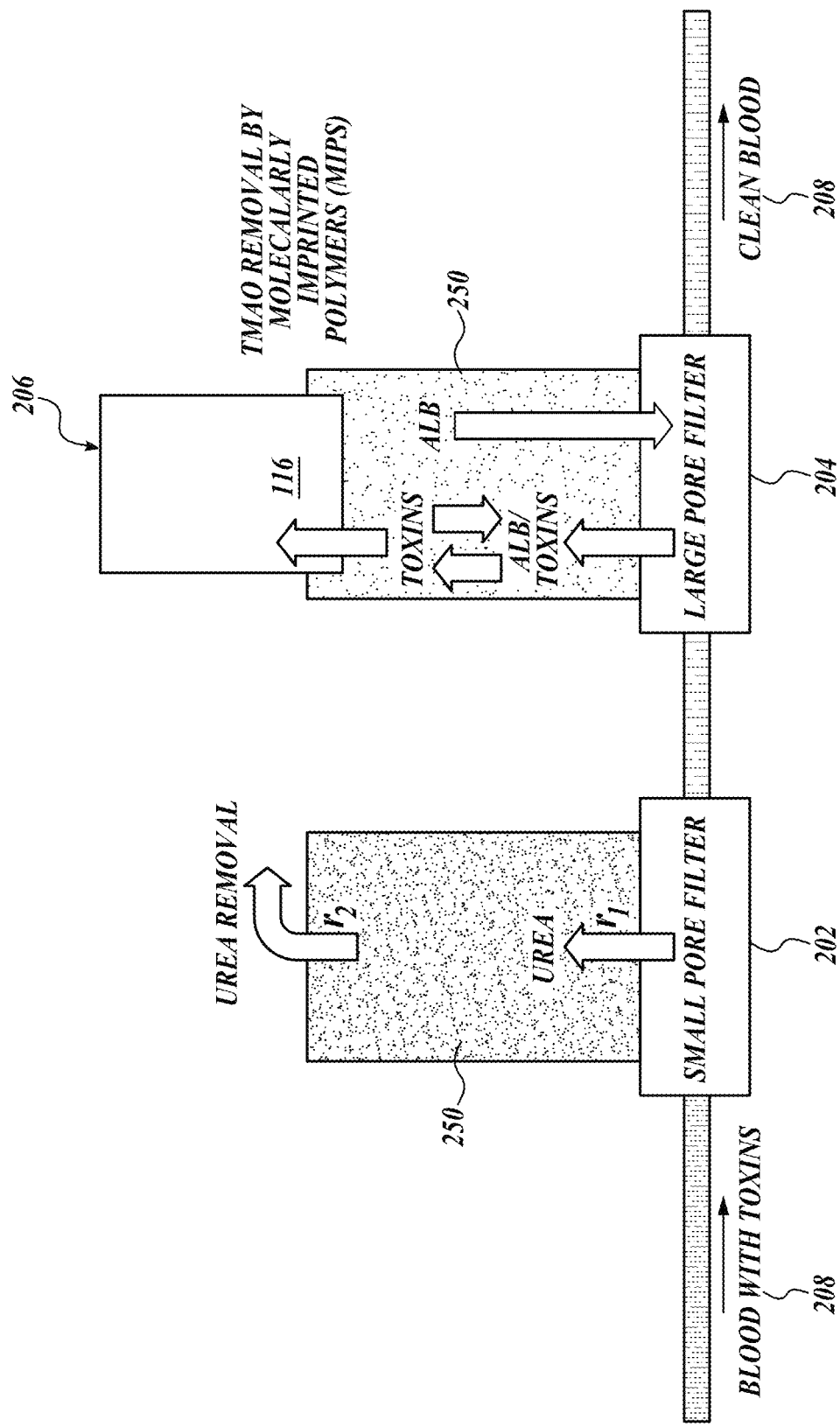
FIG. 2 is a schematic representation of an embodiment of a hemodialysis system.

The chromatography column can be a component of a hemodialysis system. The hemodialysis system can remove toxins from blood and recycle a dialysate. Referring to FIG. 2, the hemodialysis system 200 can include a small pore filter 202; a large pore filter 204; and a chromatography column or cartridge 206 including crosslinked MIP 116 of the present disclosure. In use, blood 208 containing toxins can pass through the small pore filter 202, and a dialysate 250 can remove urea. The blood 208 then further passes through a large pore filter 204; and toxins complexed to albumin can be removed from the dialysate. The TMAO in the dialysate 250 is then removed by a chromatography column or cartridge 206 including the crosslinked MIP 116 of the present disclosure.

In some embodiments, the hemodialysis system can be coupled with a non-transitory computer-readable medium having computer-executable instructions stored thereon that, if executed by one or more processors of a computing device, cause the computing device to instruct the hemodialysis system to perform one or more of the steps in a dialysis sequence.

The following Examples describe molecularly imprinted polymers, their characterization, and evaluations of their TMAO absorption properties.

EXAMPLES

Example 1

Evaluation of TMAO Absorption of MAA:EGDMA vs. Acrylamide:EGDMA TMAO-Imprinted Polymers General procedure: 300 mg polymers were put into a 20 mL scintillation vial. Then 10 mL 200 µM TMAO solution was poured into the vial. The vial was sealed with a cover and put onto a shaker for an hour for TMAO absorption. After that the remaining TMAO concentration ($C_{remaining}$) in the solution was measured by HPLC/MS using 1 mL supernatant collected from the vial. The removal efficiency was calculated as follows:

$$\text{removal efficiency} = \frac{200\mu M - C_{remaining}}{200\mu M} \times 100\%$$

TABLE 1

TMAO absorption for TMAO molecularly imprinted polymers synthesized with methacrylic acid (MAA) and ethylene glycol dimethacrylate (EGDMA).

| MAA/EGDMA Ratio | 1:9 | 1:5 | 1:1 | 2:1 | 3:1 | 4:1 | 8:1 | 11:1 | 14:1 |
|---|---|---|---|---|---|---|---|---|---|
| Removal efficiency (%) | 11.12 ± 13.4 | 19.78 + 8.01 | 47.58 ± 6.42 | 68.39 ± 5.61 | 70.75 ± 2.11 | 76.07 ± 0.58 | 78.74 ± 3.99 | 82.06 ± 3.23 | 83.56 ± 3.51 |

MIPs have better performances at increasing MAA amounts incorporated during polymer synthesis. The increase in performance started to level when MAA/EGDMA=8:1, but was best at MAA/EGDMA=14:1.

TABLE 2

TMAO absorption for TMAO molecularly imprinted polymers synthesized with acrylamide (Acry) and ethylene glycol dimethacrylate (EGDMA):

| | Acry/EGDMA ratio | | | |
|---|---|---|---|---|
| | 1:5 | 1:1 | 3:1 | 4:1 |
| Removal efficiency(%) | −1.67 ± 19.7 | −4.01 ± 6.0 | −1.53 ± 6.2 | −31.2 ± 29.8 |

As shown in Table 2 above, negative efficiency means that the remaining TMAO concentration in the supernatant was higher than the original TMAO concentration injected into vial in the beginning of the experiments. Without wishing to be bound by theory, it is believed that this phenomenon was a result of the hydrophilicity of acrylamide. Polymers containing acrylamide could absorb a large quantity of water into itself (e.g., as much as 30 times of the polymer weight itself), which can result in concentration of the TMAO solution. Thus, if polymers did not absorb TMAO, the removal efficiency will be negative. Therefore, these results demonstrate that polymers made with acrylamide and EGDMA did not function to absorb TMAO.

Example 2

MAA:EGDMA TMAO-Imprinted Polymers with Additives

TMAO molecularly imprinted polymers were synthesized with methacrylic acid (MAA) and ethylene glycol dimethacrylate (EGDMA) at a 8:1 ratio, with small amounts of additives. The absorption capacity was evaluated according to the general procedure in Example 1.

TABLE 3

TMAO absorption for acrylamide (Acry) and 2-hydroxyethyl methacrylate(HEMA)

| Additives, and molar ratio of additive to MAA | Acry 2% | Acry 4% | Acry 6% | HEMA 2% | HEMA 4% | HEMA 6% |
|---|---|---|---|---|---|---|

TABLE 3-continued

TMAO absorption for acrylamide (Acry) and
2-hydroxyethyl methacrylate(HEMA)

| Removal efficiency(%) | 81.64 ± 0.23 | 69.64 ± 2.29 | 64.98 ± 0.64 | 74.99 ± 0.64 | 71.29 ± 3.99 | 75.56 ± 1.06 |
|---|---|---|---|---|---|---|

With additives such as acrylamide and HEMA, the MIPs behaved differently. For the acrylamide additive, the removal efficiency increased when 2% acrylamide was added, compared to samples without acrylamide. However, with more acrylamide addition, the MIPs absorption drastically decreased. HEMA additives slightly decreased the MIPs' TMAO absorption ability overall, but the TMAO absorption ability did not seem to vary as a function of the amount of HEMA additive. In general, two monomer additives did not appear to improve MIPs' performance.

Example 3

MAA:EGDMA TMAO-Imprinted Polymers with Varying TMAO Template Amounts

TMAO molecularly imprinted polymers were synthesized with methacrylic acid (MAA) and ethylene glycol dimethacrylate (EGDMA) at a 8:1 ratio, with varying amounts of TMAO template in the reaction mixture. The absorption capacity was evaluated according to the general procedure in Example 1.

TABLE 4

TMAO absorption for TMAO-molecularly imprinted polymers synthesized from methacrylic acid (MAA) and ethylene glycol dimethacrylate (EGDMA) at 8:1 ratio with different amounts of TMAO template during synthesis:

| | TMAO amount | | | |
|---|---|---|---|---|
| | 110 mg (1 mmol) | 330 mg (3 mmol) | 550 mg (5 mmol) | 770 mg (7 mmol) |
| Removal efficiency(%) | 78.07 ± 0.67 | 81.34 ± 1.73 | 82.72 ± 1.36 | 81.43 ± 1.86 |

With more TMAO imprinted into the molecular imprinted polymer during polymer synthesis, the MIPs' TMAO absorption increased. The TMAO absorption saturated at around 7 mmol of TMAO imprinted in about 5 g polymer mass. Without wishing to be bound by theory, it is believed that the saturation could be related to the solubility limit of TMAO in the reaction solvent acetonitrile.

Example 4

Dimethylacrylic Acid:EGDMA TMAO-Imprinted Polymers

TMAO molecularly imprinted polymers were synthesized with 3,3-dimethylacrylic acid (MAA) and ethylene glycol dimethacrylate (EGDMA). The absorption capacity was evaluated according to the general procedure in Example 1.

To investigate additional alkyl groups' influence on the MIPs' performance, MIPs were prepared using 3,3-dimethylacrylic acid and EGDMA with 8:1 ratio.

TABLE 5

TMAO absorption for TMAO-molecularly imprinted polymers synthesized from 3,3-dimethylacrylic acid (MAA) and ethylene glycol dimethacrylate (EGDMA).

| Sample | MAA MIPs | 3,3-dimethylacrylic acid MIPs |
|---|---|---|
| Removal efficiency(%) | 78.07 ± 0.67 | 9.88 ± 9.64 |

MIPs made using 3,3-dimethylacrylic acid and ethylene glycol dimethacrylate were not as effective as the corresponding MIPS using methacrylic acid and ethylene glycol dimethacrylate.

Example 5

Microscopy of MAA:EGDMA TMAO-Imprinted Polymer Particles

Figure 3A:
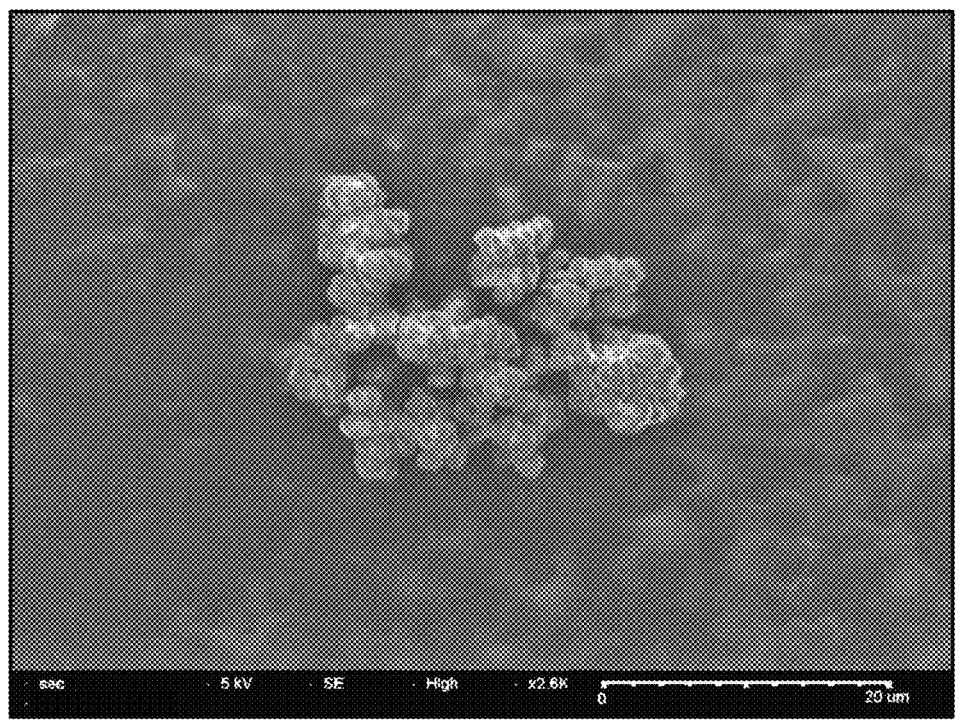
FIG. 3A is a micrograph showing an embodiment of a molecularly imprinted polymer (MIP) particle aggregate having about 20 μm maximum cross section.

Representative synthesis for bulk TMAO-MIPs (e.g., MAA/EGDMA=8:1): a desired ratio of MAA and EGDMA (e.g., for an 8:1 ratio of MAA to EGDMA:64 mmol methacrylic acid and 8 mmol ethylene glycol dimethacrylate) was added into an Erlenmeyer flask with acetonitrile (e.g., 20 mL), a quantity of TMAO (e.g., 110 mg) was added into the mixture. A radical initiator, azobisisobutyronitrile (AIBN), at 0.5% mass of the total monomers and crosslinkers (e.g., 35 mg) was added. The reaction mixture was then shaken and purged with $N_2$ for 15 min. The flask was put into a 60° C. water bath for a period of time sufficient to complete polymerization (e.g., 21 hours). A bulk molecularly imprinted polymer was obtained. The bulk polymer can be ground to provide microparticles. FIG. 3A is a scanning electron microscope image of TMAO-MIP powder with a composition of 8:1 MAA:EGDMA, the powder obtained from a ground bulk polymer. The powder was in the form of aggregates (~20 μm) of microspheres of about 2 μm diameter.

Figure 3B:
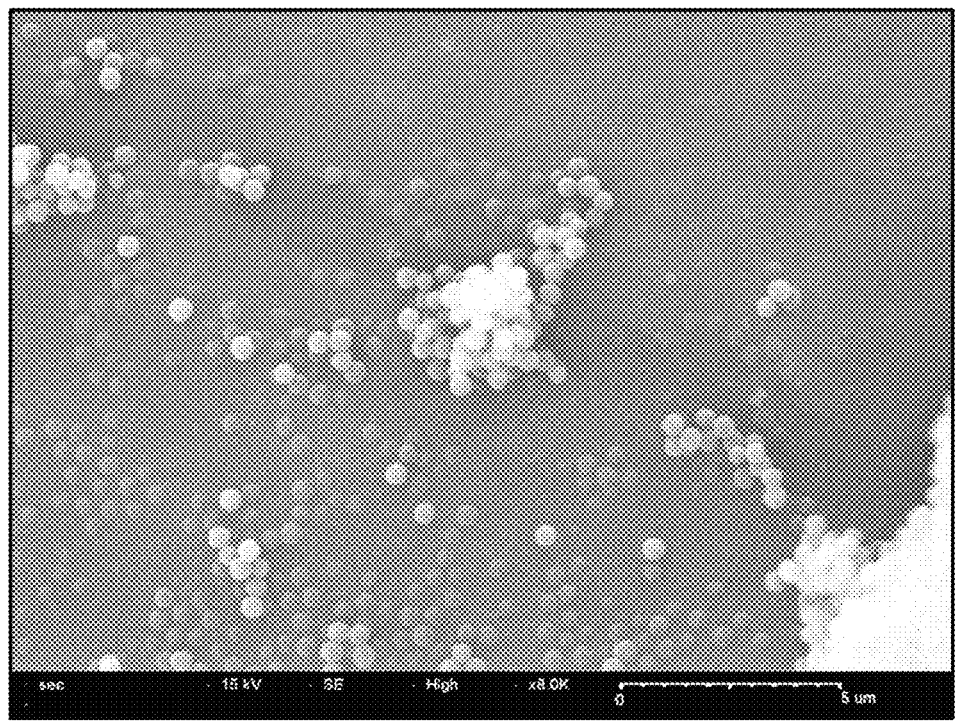
FIG. 3B is a micrograph showing an embodiment of polymer microspheres of about 2 μm diameter.

Microspherical molecularly imprinted polymers: a desired ratio of MAA and EGDMA (e.g., 6.4 mmol methacrylic acid and 0.8 mmol ethylene glycol dimethacrylate (EGDMA)) was added into a 100 mL Erlenmeyer flask with a large amount of acetonitrile (e.g., 40 mL for 6.4 mmol methacrylic acid and 0.8 mmol ethylene glycol dimethacrylate (EGDMA)). 11 mg TMAO was added into the mixture. A radical initiator, AIBN, at 0.5% mass of the total monomers and crosslinkers (e.g., 3.5 mg) was further added to the reaction mixture. The reaction mixture was then shaken and purged with $N_2$ for 15 min. The flask was put into a 60° C. water bath with constant stirring for a time sufficient to complete polymerization (e.g., 21 hours). Microspheres of a molecularly imprinted polymer were obtained. FIG. 3B is a scanning electron microscope image of TMAO-MIP microspheres with a composition of 8:1 MAA:EGDMA, generated in situ during polymerization in a dilute reaction mixture. The microspheres had a diameter of about 700 nm.

Example 6

Characterization of MAA:EGDMA TMAO-Imprinted Polymer Particles

Studies were carried out to investigate the binding behaviors over a range of TMAO concentrations and to determine the yield disassociation constant for the binding between MIPs and TMAO.

10 mL of 10 µM, 25 µM, 100 µM, 200 µM, 500 µM and 1000 µM TMAO solutions were added into 7 vials, each with 60 mg TMAO MIPs. Then the vials were put onto a shaker for one hour to establish equilibrium between the MIPs and TMAO solution. Supernatants from each vial were collected and the remaining TMAO concentration in the supernatant was measured with HPLC-MS. TMAO absorption capacity was calculated to be $$\text{absorption capacity} = \frac{(C_{beginning} - C_{remaining}) * V_{TMAO} * M_{TMAO}}{\text{polymermass}}$$

where $C_{beginning}$ is the original TMAO concentration added into the vial. $C_{remaining}$ is the concentration of TMAO in the supernatant. $M_{TMAO}$ is the molar mass of TMAO (75.11 g/mol) and $V_{TMAO}$ is the volume of TMAO solutions added into the vial (10 mL). Polymer mass is the mass of the MIPs put into the vial (60 mg).

Figure 4:
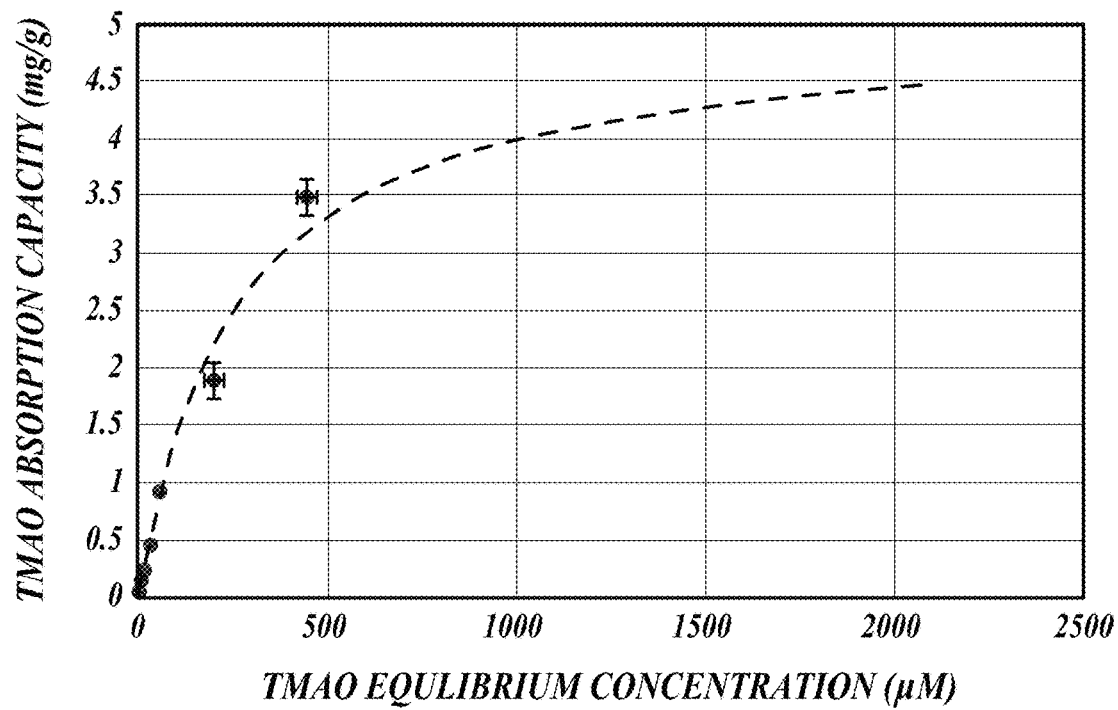
FIG. 4 is a graph showing TMAO absorption capacity over a range of TMAO equilibrium concentrations for an embodiment of TMAO MIP of the present disclosure, having a MAA to EGDMA ratio of 8:1.

FIG. 4 shows the absorption capacity of TMAO MIPs with MAA/EGDMA=8:1 over a range of TMAO equilibrium concentration. The formula below describes the isotherm curve, where the calculated disassociation constant for binding between MIPs and TMAO is 250 µM and the maximum capacity of TMAO MIPs is 5 mg/g.

$$\text{absorption capacity} = \frac{capacity_{max} * [TMAO]_{eq}}{[TMAO]_{eq} + K_d}$$

In the formula, $K_d$ is the disassociation constant for binding between MIPs and TMAO and $capacity_{max}$ is the maximum TMAO absorption capacity for MIPs. $[TMAO]_{eq}$ is the concentration of TMAO at equilibrium.

The amount of water the polymer can absorb can be assessed by determining the swelling ratio, which is defined as the fractional increase in the weight of the polymer due to water absorption:

$$\text{swelling ratio} = \frac{W_s - W_d}{W_d}$$

where Ws is the polymer weight saturated with water and Wd is the polymer dry weight. The swelling ratio of a 8:1 MAA:EGDMA TMAO-imprinted polymer was 3.20.

Example 7

Flow and Static Absorption Evaluation of MAA:EGDMA TMAO-Imprinted Polymer Particles Evaluation of Molecularly Imprinted Polymer Capacity Under Static Conditions Experimental procedures: 300 mg polymers were put into a 20 mL scintillation vial. Then 10 mL 200 µM TMAO solution was poured into the vial. The vial was sealed with cover and put onto a shaker for an hour to allow TMAO absorption approaching equilibrium. After that the remaining TMAO concentration $C_{remaining}$ in the solution was measured by HPLC/MS with 1 mL supernatant collected from the vial. The removal efficiency is calculated as follows:

$$\text{removal efficiency} = \frac{200\mu M - C_{remaining}}{200\mu M} \times 100\%$$

All experiments were done in triplicates.

Figure 5:
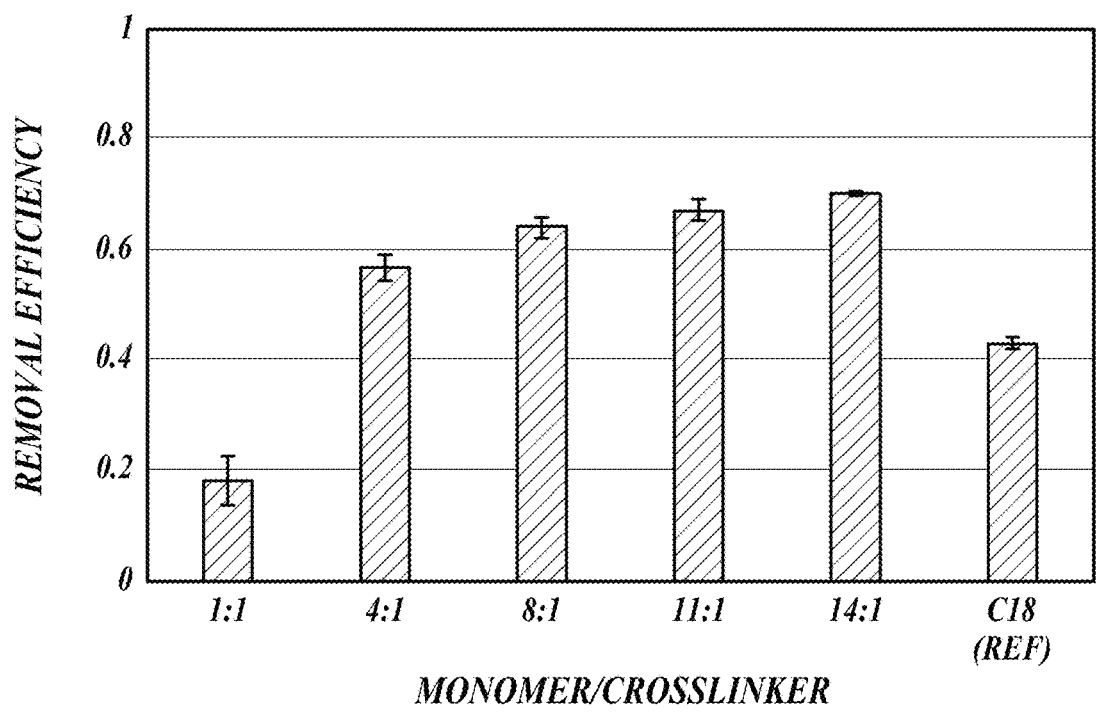
FIG. 5 a bar graph showing a static absorption test of TMAO by embodiments of MIPs of the present disclosure, having various molar ratios of monomer methacrylic acid (MAA) to crosslinker (EGDMA).

FIG. 5 shows the results from static absorption tests of TMAO by MIPs with various molar ratios of monomer methacrylic acid (MAA) to crosslinker (EGDMA).

Evaluation of Molecularly Imprinted Polymer Capacity Under Flow Conditions

Figure 6:
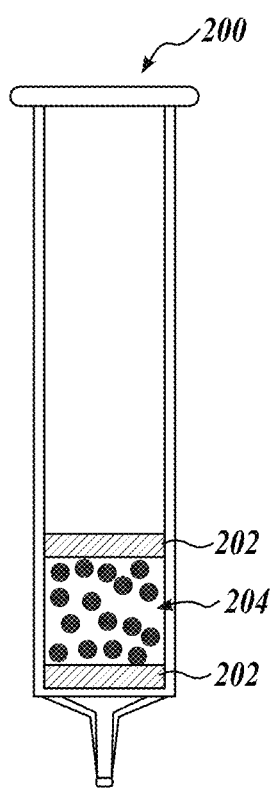
FIG. 6 is an illustration of an example of a chromatography column of the present disclosure.

Experimental procedures: 0.5 g polymers were packed into a 60 mL syringe between two frits as shown in FIG. 6. Briefly, one frit was positioned into the bottom of the syringe. 0.5 g of polymer particles was added into the syringe. Another frit was placed on top of the polymer to seal the polymer particles between the two frits. The upper frit was pressed down to tightly pack the polymer particles. Test solution can be continuously flowed through the syringe column under flow conditions for evaluation of absorption capacity of a given MIP. To regenerate the column, deionized water was continuously flowed through the syringe column until all TMAO absorbed onto the column was fully desorped. The amount of water to use was found to be 300 mL water per 500 mg polymers.

To evaluate absorption capacity, TMAO solution of 200 µM continued to flow through the syringe. 1 mL supernatant coming out of the syringe was collected at every 50 mL. The remaining TMAO concentration $C_{remaining}$ in the supernatant was measured via HPLC/MS. The removal efficiency is calculated as follows:

$$\text{removal efficiency} = \frac{200\mu M - C_{remaining}}{200\mu M} \times 100\%$$

The capacity was further calculated with the formula:

$$\text{capacity} = \frac{Area_{underthecurve} \times M_{TMAO}}{\text{polymermass}}$$

Where $M_{TMAO}$ is the molecular weight of the TMAO (75.11 g/mol), polymer mass used in this experiment is 0.5 g.

Figure 7A:
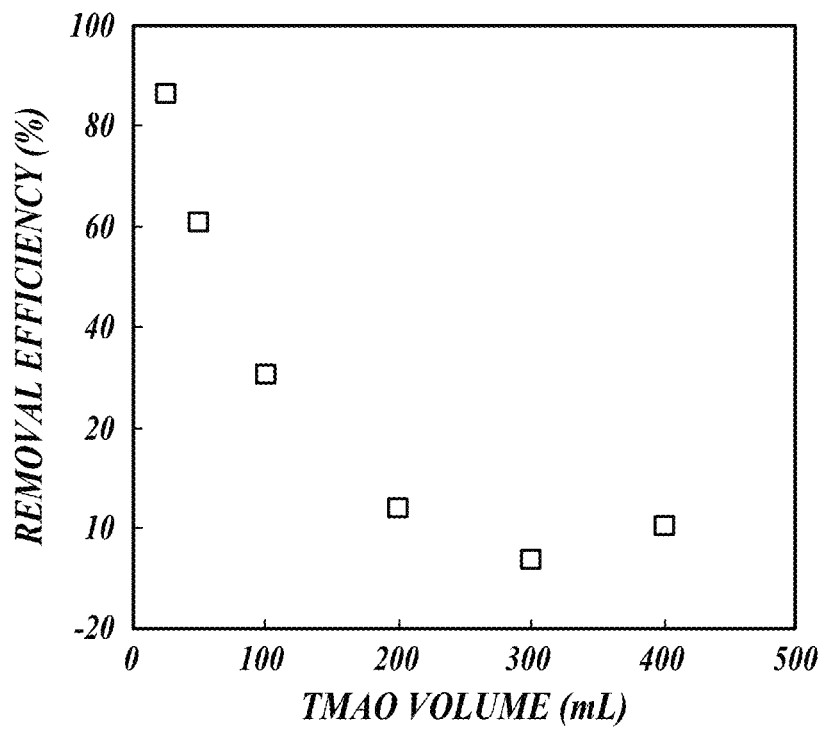
FIG. 7A is a graph showing TMAO absorption under flow conditions for an embodiment of a MIP of the present disclosure (monomer to crosslinker=8:1).
Figure 7B:
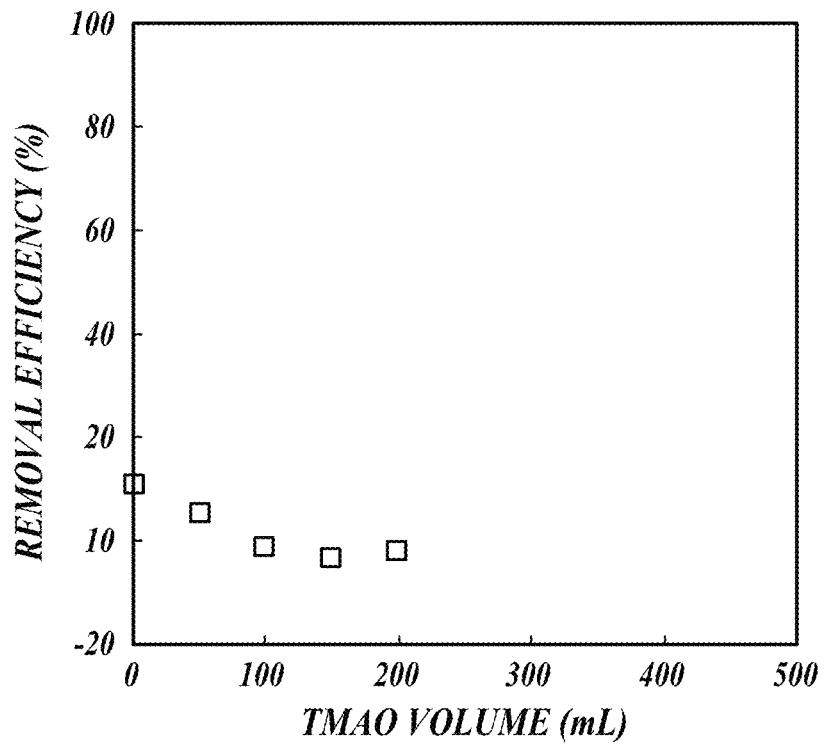
FIG. 7B is a graph showing TMAO absorption under flow conditions for a C18 reference resin.

FIGS. 7A and 7B are graphs showing TMAO absorption under flow conditions for MIPs (MAA:EGDMA=8:1) and a C18 reference resin. The TMAO solution was 200 µM, the experiment was conducted at a flow rate of 5 mL/min. The absorption capacity was calculated (the area under the curve) to be 1.05 mg/g for MIP and <0.1 mg/g for the C18 reference resin.

Thus, TMAO removal efficiency of molecularly imprinted polymers increases with higher monomer-to-crosslinker ratio. It is believed that the increase of capacity is likely due to the increase of the number of available binding sites. The MIPs had much higher capacity than the C18 reference. The absorption capacity of the a 8:1 monomer to crosslinker MIP was measured to be 1.05 mg/g while the C18 reference had only less than 0.1 mg/g capacity. With such absorption capacity, only about 200 g of MIPs may be required to absorb all the TMAO cleared during one typical dialysis (~160 mg). The MIPs of the present disclosure were more selective for TMAO over DMSO.

The TMAO absorption capacity was also evaluated for a range of flow rates. When the syringe for the column pack is 5 mL and polymer usage is 0.5 g, the absorption capacities for different flow rates is indicated in Table 6.

TABLE 6

Absorption capacity for MIPs of MAA/EGDMA = 8:1.

| | Flow rates | | | |
|---|---|---|---|---|
| | 1 mL/min | 5 mL/min | 10 mL/min | 20 mL/min |
| Capacity(mg/g) | 0.975 | 1.125 | 0.923 | 1.025 |

The TMAO absorption capacity under flow conditions was stable over a range of moderate flow rates.

Example 8

Competitive Test of TMAO and DMSO

Experimental procedures: 300 mg polymers were put into a 20 mL scintillation vial. Then 10 mL solution of 200 µM TMAO and 200 µM dimethyl sulfoxide (DMSO) was poured into the vial. The vial was sealed with cover and put onto a shaker for an hour to allow equilibrium achieved. After that the remaining TMAO concentration $C_{TMAO}$ and DMSO concentration $C_{DMSO}$ in the solution was measured by HPLC/MS with 1 mL supernatant collected from the vial. The removal efficiency for each compound was calculated as follows:

$$TMAO \text{ removal efficiency} = \frac{200\mu M - C_{TMAO}}{200\mu M} \times 100\%$$

$$DMSO \text{ removal efficiency} = \frac{100\mu M - C_{DMSO}}{200\mu M} \times 100\%$$

Figure 8:
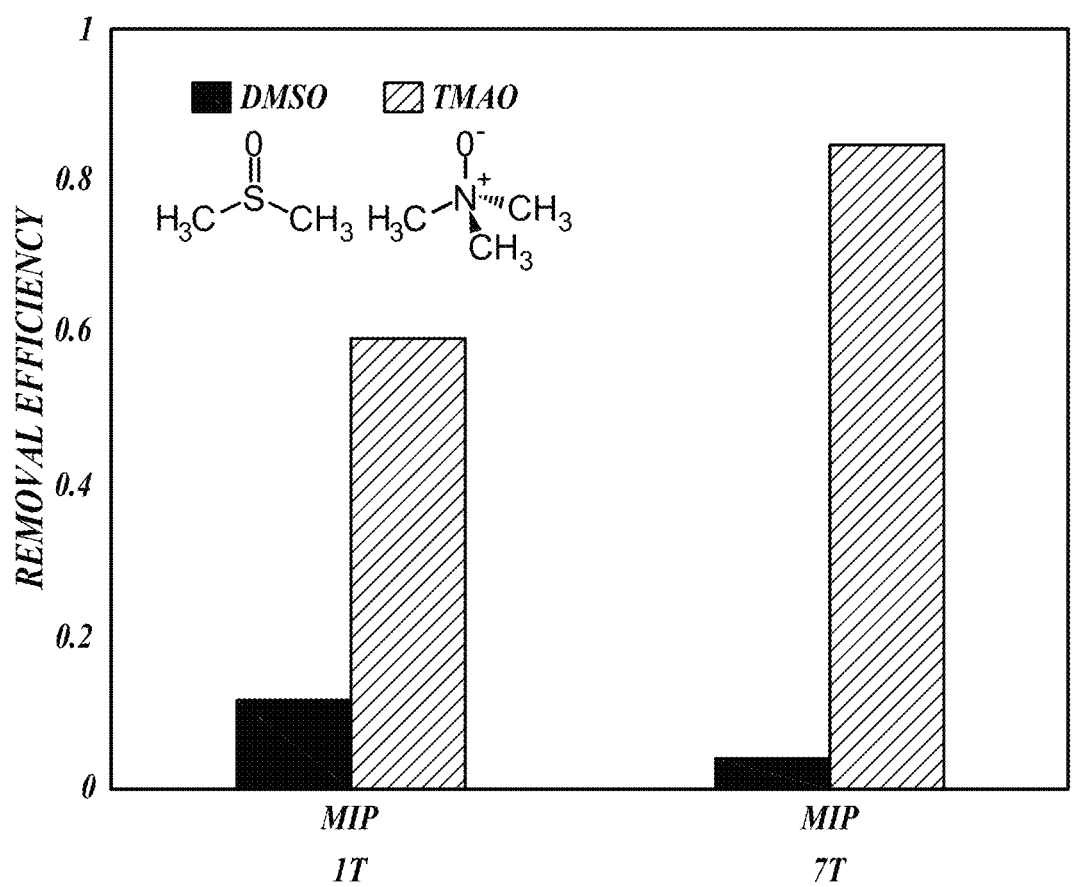
FIG. 8 is a bar graph showing competitive binding assay of TMAO vs. DMSO by embodiments of MIPs of the present disclosure (1T=1 mmol of TMAO template addition during polymer synthesis, 7T=7 mmol of TMAO template addition during polymer synthesis).

FIG. 8 is a bar graph showing the competitive binding of TMAO and DMSO by a MIP having an 8:1 ratio of MAA to EGDMA. Table 7 shows the quantitative values of removal efficiency of the polymer for TMAO and DMSO at 1 mmol of TMAO addition during synthesis, and at 7 mmol of TMAO addition during synthesis (also shown graphically in FIG. 8).

TABLE 7

Removal efficiency of MAA:EGDMA for TMAO and DMSO

| Sample and target molecule | TMAO 1T DMSO | TMAO 1T TMAO | TMAO 7T DMSO | TMAO 7T TMAO |
|---|---|---|---|---|
| Removal efficiency(%) | 11.80 | 59.58 | 3.80 | 85.14 |

MIPs for TMAO were successfully synthesized. MIPs show 2 orders of magnitude higher absorption capacity towards TMAO over common nonspecific sorbents, for example C18. MIPs for TMAO also demonstrate a binding preference for TMAO over DMSO. MIPs developed have potential to be used in portable hemodialysis machines for the specific removal of TMAO toxin.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of making a crosslinked polymer, comprising:
    polymerizing a monomer comprising a ($C_{0-6}$alkyl)acrylic acid, di($C_{1-6}$alkyl)acrylic acid, or a combination thereof; and a crosslinker comprising a ($C_{1-6}$ alkylene glycol)-di($C_{1-6}$alkyl)acrylate, trimethylolpropane trimethacrylate, N,N'-methylenebisacrylamide, or any combination thereof; at a monomer:crosslinker ratio of from 1:9 to 14:1, in the presence of trimethylamine N-oxide and a solvent, to provide the crosslinked polymer,
    wherein the crosslinked polymer comprises specific binding sites for trimethylamine N-oxide and a trimethylamine N-oxide absorption capacity of at least 0.5 mg/g.

2. The method of claim 1, further comprising grinding the crosslinked polymer to form the plurality of particles of the crosslinked polymers.

3. The method of claim 1, wherein polymerizing the monomer and the crosslinker is in solution at a concentration of less than 180 mM to form a plurality of particles of the crosslinked polymers.

4. The method of claim 1, wherein the solvent is selected from acetonitrile, methanol, water, dialysate solution, or any combination thereof.

5. The method of claim 1, further comprising a radical initiator.

\* \* \* \* \*